United States Patent
Volkar et al.

(10) Patent No.: US 11,529,456 B2
(45) Date of Patent: Dec. 20, 2022

(54) ACOUSTIC FREQUENCY RECOGNITION OF PATIENT LINES

(71) Applicant: BAYER HEALTHCARE LLC, Whippany, NJ (US)

(72) Inventors: John Volkar, Valencia, PA (US); Corey Kemper, Pittsburgh, PA (US); Richard Dotson, Verona, PA (US); Bernard Hobi, Jeannette, PA (US)

(73) Assignee: Bayer Healthcare LLC, Whippany, NJ (US)

( * ) Notice: Subject to any disclaimer, the term of this patent is extended or adjusted under 35 U.S.C. 154(b) by 644 days.

(21) Appl. No.: 16/481,916

(22) PCT Filed: Jan. 29, 2018

(86) PCT No.: PCT/US2018/015666
§ 371 (c)(1),
(2) Date: Jul. 30, 2019

(87) PCT Pub. No.: WO2018/144369
PCT Pub. Date: Aug. 9, 2018

(65) Prior Publication Data
US 2020/0038580 A1 Feb. 6, 2020

Related U.S. Application Data

(60) Provisional application No. 62/453,130, filed on Feb. 1, 2017.

(51) Int. Cl.
*A61M 5/00* (2006.01)
*A61M 5/14* (2006.01)
*A61M 5/168* (2006.01)

(52) U.S. Cl.
CPC .......... *A61M 5/007* (2013.01); *A61M 5/1409* (2013.01); *A61M 5/16827* (2013.01);
(Continued)

(58) Field of Classification Search
CPC ................ A61M 5/007; A61M 5/1409; A61M 5/16827; A61M 5/16811; A61M 5/16831;
(Continued)

(56) References Cited

U.S. PATENT DOCUMENTS 7,925,330 B2   4/2011   Kalafut et al.
7,937,134 B2   5/2011   Uber et al.
(Continued)

FOREIGN PATENT DOCUMENTS

WO   2008083313 A2   7/2008
WO   2009149367 A1   12/2009
(Continued)

OTHER PUBLICATIONS

"International Preliminary Report on Patentability from PCT Application No. PCT/US2018/015666", dated Aug. 15, 2019.
(Continued)

*Primary Examiner* — Nathan R Price
*Assistant Examiner* — Anh Bui
(74) *Attorney, Agent, or Firm* — James R. Stevenson; David Schramm; Joseph L. Kent

(57) ABSTRACT

A fluid injector system includes a powered fluid injector, a connection port configured to receive a single-use disposable set having tubing connected to a fluid inlet port at a first end and connected to a waste outlet port at a second end, and a detector associated with the connection port and configured to generate a signal in response to a sonic, infrasonic, or ultrasonic wave emitted from the single-use disposable set during a priming operation of the single-use disposable set. In some examples, the detector is configured to generate a signal if the frequency of the wave emitted from the single-use disposable set is outside a predetermined range of frequencies corresponding to a predetermined range of frequencies of air expelled from the tubing. A method for detecting the multiple uses of a single-use disposable set connected to a fluid injector system is also provided.

20 Claims, 11 Drawing Sheets

(52) U.S. Cl.
CPC . *A61M 5/16881* (2013.01); *A61M 2005/1402* (2013.01); *A61M 2205/18* (2013.01); *A61M 2205/3375* (2013.01); *A61M 2205/50* (2013.01); *A61M 2205/502* (2013.01); *A61M 2205/581* (2013.01); *A61M 2205/587* (2013.01)

(58) Field of Classification Search
CPC ........ A61M 5/5086; A61M 2005/1402; A61M 2005/1588; A61M 2205/18; A61M 2205/3375; A61M 2205/50; A61M 2205/502; A61M 2205/581; A61M 2205/587; A61M 2205/14; A61M 2205/3306; A61M 2205/583
See application file for complete search history.

(56) References Cited

U.S. PATENT DOCUMENTS

| | | |
|---|---|---|
| 8,133,203 B2 | 3/2012 | Hack |
| 8,160,679 B2 | 4/2012 | Uber et al. |
| 8,521,716 B2 | 8/2013 | Uber, III et al. |
| 9,056,200 B2 | 6/2015 | Uber, III et al. |
| 9,474,857 B2 | 10/2016 | Riley et al. |
| 9,750,953 B2 | 9/2017 | Kalafut |
| 9,913,941 B2 | 3/2018 | Miller et al. |
| 2006/0226087 A1* | 10/2006 | Robinson .............. B04B 5/0442 210/512.1 |
| 2008/0183131 A1 | 7/2008 | Duchon et al. |
| 2010/0262078 A1 | 10/2010 | Blomquist |
| 2016/0331951 A1* | 11/2016 | Sokolov ............. A61M 39/1011 |
| 2017/0258982 A1 | 9/2017 | Kemper |
| 2017/0343446 A1 | 11/2017 | Ciolkosz et al. |
| 2018/0015274 A1* | 1/2018 | Haury ................. A61M 5/1407 |
| 2019/0224407 A1* | 7/2019 | Savio ..................... A61M 5/20 |

FOREIGN PATENT DOCUMENTS

| | | |
|---|---|---|
| WO | 2015106107 A1 | 7/2015 |
| WO | 2016112163 A1 | 7/2016 |
| WO | 2018144369 A1 | 8/2018 |

OTHER PUBLICATIONS

"International Search Report and Written Opinion from PCT Application No. PCT/US2018/015666", dated Jun. 11, 2018.

* cited by examiner

ACOUSTIC FREQUENCY RECOGNITION OF PATIENT LINES

CROSS REFERENCE TO RELATED APPLICATIONS

The present application is a 371 national phase application of International (PCT) Application No. PCT/US2018/015666, filed Jan. 29, 2018, and claims the benefit of U.S. Provisional Patent Application No. 62/453,130, filed Feb. 1, 2017, entitled "Acoustic Frequency Recognition of Patient Lines", the disclosure of which is hereby incorporated by reference in its entirety.

BACKGROUND OF THE DISCLOSURE

Field of the Disclosure

The present disclosure relates generally to single-use disposable set connectors configured for delivering medical fluid to a patient. More specifically, the disclosure relates to acoustic frequency recognition of single-use disposable set connectors for use with automatic fluid injector systems.

Description of the Related Art

In many medical diagnostic and therapeutic procedures, a medical practitioner, such as a physician, injects a patient with one or more medical fluids. In recent years, a number of medical fluid delivery systems for pressurized injection of fluids, such as a contrast solution (often referred to simply as "contrast"), a flushing agent, such as saline, and other medical fluids, have been developed for use in procedures such as angiography, computed tomography (CT), ultrasound, magnetic resonance imaging (MRI), positron emission tomography (PET), and other molecular imaging procedures. In general, these medical fluid delivery systems are designed to deliver a preset amount of fluid at a preset flow rate.

In some injection procedures, the medical practitioner places a catheter or needle into a vein or artery of the patient. The catheter or needle is connected to either a manual or an automatic fluid injector system by way of tubing and a connector that interfaces with the fluid injector system. Automatic fluid injector systems typically include at least one syringe connected to at least one fluid injector having, for example, a powered linear piston. The at least one syringe includes, for example, a source of contrast and/or a source of flushing fluid. The medical practitioner enters settings into an electronic control system of the fluid injector for a fixed volume of contrast and/or saline and a fixed rate of injection for each. A single-use disposable set connector and associated tubing are connected to the fluid injector system for delivering one or more fluids to the patient.

To prevent contamination between patients and medical devices, each single-use disposable set connector and associated tubing is ideally replaced between patients. However, users may be inclined to reuse single-use disposable set connectors to save time and cost, an unhygienic and potentially dangerous practice.

While various manual and automatic fluid delivery systems are known in the medical field, improved multi-fluid delivery systems adapted for use in medical diagnostic and therapeutic procedures where one or more fluids are supplied to a patient during such procedures continue to be in demand. Additionally, improved single-use disposable set connectors that may be used with multi-fluid delivery systems for facilitating a delivery of one or more fluids to a patient are also desired in the medical field. In particular, there exists a need for fluid delivery systems and single-use disposable set connectors which encourage and enforce safe and hygienic work practices.

SUMMARY OF DISCLOSURE

The present disclosure generally relates to a fluid injector system including a detector for detecting whether a single-use disposable set has been used for multiple fluid injection operations. Additionally, the present disclosure generally relates to a method for detecting multiple uses of a single-use disposable set connected to a fluid injector system.

In some examples, the present disclosure is directed to a fluid injector system including a powered fluid injector, a connection port configured to receive a single-use disposable set having tubing connected to a fluid inlet port at a first end and connected to a waste outlet port at a second end, and a detector associated with the connection port and configured to generate a signal in response to a sonic, infrasonic, or ultrasonic wave emitted from the single-use disposable set during a priming operation of the single-use disposable set.

In some examples, the detector is configured to generate a signal if the frequency of the sonic, infrasonic, or ultrasonic wave emitted from the single-use disposable set is outside a predetermined range of frequencies, the predetermined range of frequencies corresponding to a predetermined range of frequencies of air expelled from the tubing during the priming operation.

In some examples, the fluid injector system further includes an indicator configured to receive the signal generated by the detector, and, based on the received signal, generate an alert.

In some examples, the indicator includes a light and generating the alert includes illuminating the light.

In some examples, the indicator includes a speaker and generating the alert includes emitting an audible sound from the speaker.

In some examples, the fluid injector system further includes an electronic control device configured to control filling and delivery operations of the powered fluid injector, the electronic control device including at least one processor programmed or configured to receive the signal generated by the detector. The signal generated by the detector includes frequency data of the sonic, infrasonic, or ultrasonic wave emitted from the single-use disposable set during the priming operation.

In some examples, the at least one processor of the electronic control device is further programmed or configured to determine, based on the frequency data, whether the frequency of the sonic, infrasonic, or ultrasonic wave emitted from the single-use disposable set is outside a predetermined range of frequencies, the predetermined range of frequencies corresponding to a predetermined range of frequencies of air expelled from the tubing during the priming operation. The at least one processor of the electronic control device is further programmed or configured to determine, if the frequency of the sonic, infrasonic, or ultrasonic wave emitted from the single-use disposable set is outside the predetermined range of frequencies, whether the single-use disposable set was used during a fluid injection procedure prior to the priming operation.

In some examples, the at least one processor of the electronic control device is further programmed or configured to determine, based on a duration of the sonic, infrasonic, or ultrasonic wave, a length of the tubing.

In some examples, the at least one processor of the electronic control device is further programmed or configured to determine, based on at least one of the length of the tubing and the duration of the sonic, infrasonic, or ultrasonic wave, an amount of fluid necessary to prime the single-use disposable set.

In some examples, the fluid injector system further includes a user interface having a display. The at least one processor of the electronic control device is further programmed or configured to display a message on the user interface if the at least one processor determines that the single-use disposable set was used during a fluid injection procedure prior to the priming operation.

In some examples, the at least one processor of the electronic control device is further programmed or configured to prevent a subsequent fluid injection procedure if the at least one processor determines that the single-use disposable set was used during a fluid injection procedure prior to the priming operation.

In some examples, the at least one processor of the electronic control device is further programmed or configured to store a data entry on a computer-readable media if the at least one processor determines that the single-use disposable set was used during a fluid injection procedure prior to the priming operation.

In some examples, the data entry includes a time at which the priming operation of the single-use disposable set was performed.

In some examples, the data entry includes identification information of a user of the fluid injector system.

In some examples, the at least one processor of the electronic control device is further programmed or configured to permit a subsequent fluid injection procedure if the at least one processor determines that the single-use disposable set was not used during a fluid injection procedure prior to the priming operation.

In some examples, the present disclosure is directed to a method for detecting multiple uses of a single-use disposable set connected to a fluid injector system. The method includes priming the single-use disposable set with a medical fluid, detecting the at least one of the frequency and duration of a sonic, infrasonic, or ultrasonic wave emitted from the single-use disposable set during the priming operation, and determining, based on at least one of the frequency and duration of the sonic, infrasonic, or ultrasonic wave, whether air is expelled from the single-use disposable set during the priming operation.

In some examples, the method further includes generating an alert if the frequency of the sonic, infrasonic, or ultrasonic wave is outside a predetermined range of frequencies, the predetermined range of frequencies corresponding to a predetermined range of frequencies of air expelled from the single-use disposable set.

In some examples, the alert includes a message displayed on a user interface of the fluid injection system.

In some examples, the method further includes preventing a subsequent fluid injection procedure if the frequency of the sonic, infrasonic, or ultrasonic wave is outside a predetermined range of frequencies, the predetermined range of frequencies corresponding to a predetermined range of frequencies of air expelled from the single-use disposable set.

In some examples, the method further includes storing, on a computer-readable media, a data entry if the frequency of the sonic, infrasonic, or ultrasonic wave is outside a predetermined range of frequencies, the predetermined range of frequencies corresponding to a predetermined range of frequencies of air expelled from the single-use disposable set.

In accordance with other examples, the disclosure of the present application may be characterized by one or more of the following clauses:

Clause 1: A fluid injector system, comprising: a powered fluid injector; a connection port configured to receive a single-use disposable set, the single-use disposable set having tubing connected to a fluid inlet port at a first end and connected to a waste outlet port at a second end; and a detector associated with the connection port and configured to generate a signal in response to a sonic, infrasonic, or ultrasonic wave emitted from the single-use disposable set during a priming operation of the single-use disposable set.

Clause 2: The fluid injector system of clause 1, wherein the detector is configured to generate a signal if the frequency of the sonic, infrasonic, or ultrasonic wave emitted from the single-use disposable set is outside a predetermined range of frequencies, the predetermined range of frequencies corresponding to a predetermined range of frequencies of air expelled from the tubing during the priming operation.

Clause 3: The fluid injector system of clause 1 or 2, further comprising an indicator configured to: receive the signal generated by the detector; and based on the received signal, generate an alert.

Clause 4: The fluid injector system of any of clauses 1 to 3, wherein the indicator comprises a light and wherein generating the alert comprises illuminating the light.

Clause 5: The fluid injector system of any of clauses 1 to 4, wherein the indicator comprises a speaker and wherein generating the alert comprises emitting an audible sound from the speaker.

Clause 6: The fluid injector system of any of clauses 1 to 5, further comprising: an electronic control device configured to control filling and delivery operations of the powered fluid injector, the electronic control device comprising at least one processor programmed or configured to receive the signal generated by the detector, wherein the signal generated by the detector comprises frequency data of the sonic, infrasonic, or ultrasonic wave emitted from the single-use disposable set during the priming operation.

Clause 7: The fluid injector system of any of clauses 1 to 6, wherein the at least one processor of the electronic control device is further programmed or configured to: determine, based on the frequency data, whether the frequency of the sonic, infrasonic, or ultrasonic wave emitted from the single-use disposable set is outside a predetermined range of frequencies, the predetermined range of frequencies corresponding to a predetermined range of frequencies of air expelled from the tubing; and determine, if the frequency of the sonic, infrasonic, or ultrasonic wave emitted from the single-use disposable set is outside the predetermined range of frequencies, whether the single-use disposable set was used during a fluid injection procedure prior to the priming operation.

Clause 8: The fluid injector system of any of clauses 1 to 7, wherein the at least one processor of the electronic control device is further programmed or configured to determine, based on a duration of the sonic, infrasonic, or ultrasonic wave, a length of the tubing.

Clause 9: The fluid injector system of any of clauses 1 to 8, wherein the at least one processor of the electronic control device is further programmed or configured to determine, based on at least one of the length of the tubing and the duration of the sonic, infrasonic, or ultrasonic wave, an amount of fluid necessary to prime the single-use disposable set.

Clause 10: The fluid injector system of any of clauses 1 to 9, further comprising a user interface having a display, wherein the at least one processor of the electronic control device is further programmed or configured to display a message on the user interface if the at least one processor determines that the single-use disposable set was used during a fluid injection procedure prior to the priming operation.

Clause 11: The fluid injector system of any of clauses 1 to 10, wherein the at least one processor of the electronic control device is further programmed or configured to prevent a subsequent fluid injection procedure if the at least one processor determines that the single-use disposable set was used during a fluid injection procedure prior to the priming operation.

Clause 12: The fluid injector system of any of clauses 1 to 11, wherein the at least one processor of the electronic control device is further programmed or configured to: store a data entry on a computer-readable media if the at least one processor determines that the single-use disposable set was used during a fluid injection procedure prior to the priming operation.

Clause 13: The fluid injector system of any of clauses 1 to 12, wherein the data entry comprises a time at which the priming operation was performed.

Clause 14: The fluid injector system of any of clauses 1 to 13, wherein the data entry comprises identification information of a user of the fluid injector system.

Clause 15: The fluid injector system of any of clauses 1 to 14, wherein the at least one processor of the electronic control device is further programmed or configured to permit a subsequent fluid injection procedure if the at least one processor determines that the single-use disposable set was not used during a fluid injection procedure prior to the priming operation.

Clause 16: A method for detecting multiple uses of a single-use disposable set connected to a fluid injector system, the method comprising: priming the single-use disposable set with a medical fluid; detecting at least one of the frequency and duration of a sonic, infrasonic, or ultrasonic wave emitted from the single-use disposable set during the priming operation; and determining, based on at least one of the frequency and duration of the sonic, infrasonic, or ultrasonic wave, whether air is expelled from the single-use disposable set during the priming operation.

Clause 17: The method of clause 16, further comprising generating an alert if the frequency of the sonic, infrasonic, or ultrasonic wave is outside a predetermined range of frequencies, the predetermined range of frequencies corresponding to a predetermined range of frequencies of air expelled from the single-use disposable set.

Clause 18: The method of clause 16 or 17, wherein the alert comprises a message displayed on a user interface of the fluid injection system.

Clause 19: The method of any of clauses 16 to 18, further comprising preventing a subsequent fluid injection procedure if the frequency of the sonic, infrasonic, or ultrasonic wave is outside a predetermined range of frequencies, the predetermined range of frequencies corresponding to a predetermined range of frequencies of air expelled from the single-use disposable set.

Clause 20: The method of any of clauses 16 to 19, further comprising storing, on a computer-readable media, a data entry if the frequency of the sonic, infrasonic, or ultrasonic wave is outside a predetermined range of frequencies, the predetermined range of frequencies corresponding to a predetermined range of frequencies of air expelled from the single-use disposable set.

These and other features and characteristics of single-use disposable set connectors for delivering medical fluid to a patient, as well as the methods of operation and functions of the related elements of structures and the combination of parts and economies of manufacture, will become more apparent upon consideration of the following description and the appended claims with reference to the accompanying drawings, all of which form a part of this specification. It is to be expressly understood, however, that the drawings are for the purpose of illustration and description only.

DETAILED DESCRIPTION

Figure 1:
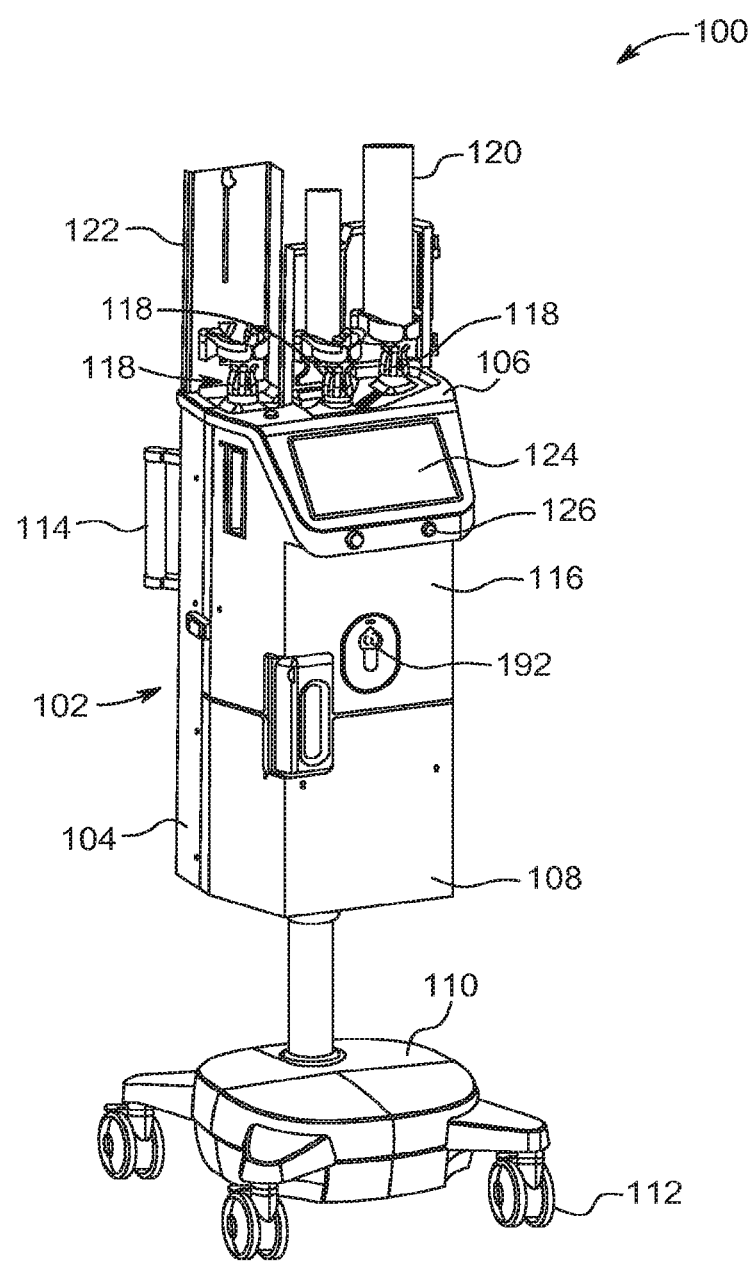
FIG. 1 is a perspective view of a multi-fluid delivery system, according to one example.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. When used in relation to a syringe of a multi-patient disposable set, the term "proximal" refers to a portion of a syringe nearest a piston element for delivering fluid from a syringe. When used in relation to a single-use disposable set connector, the term "distal" refers to a portion of a single-use disposable set connector nearest to a user when a single-use disposable set connector is oriented for connecting with a multi-fluid injector system. When used in relation to a syringe of a, the term "distal" refers to a portion of a syringe nearest to a delivery nozzle. When used in relation to a single-use disposable set connector, the term "proximal" refers to a portion of a single-use disposable set connector nearest to a multi-fluid injector system when a single-use disposable set connector is oriented for connecting with a multi-fluid injector system.

As used herein, the terms "acoustic" and "acoustic frequency" refer to a sonic, infrasonic, or ultrasonic wave or waves which may be within, below, or above the range of human audibility.

It is also to be understood that the specific devices and processes illustrated in the attached drawings, and described in the following specification, are simply exemplary examples of the disclosure. Hence, specific dimensions and other physical characteristics related to the examples disclosed herein are not to be considered as limiting.

Referring to the drawings in which like reference characters refer to like parts throughout the several views thereof, the present disclosure is generally directed to a multi-fluid medical injector/injection system 100 (hereinafter "fluid injector system 100") having a multi-patient disposable set (MUDS) 130 configured for delivering fluid to a patient using a single-use disposable set (SUDS) 190 connector. The fluid injector system 100 includes multiple components as individually described herein. Generally, the fluid injector system 100 has a powered injector or other administration device and a fluid delivery set intended to be associated with the injector to deliver one or more fluids from one or more multi-dose containers under pressure into a patient, as described herein. The various devices, components, and features of the fluid injector system 100 and the fluid delivery set associated therewith are likewise described in detail herein.

With reference to FIG. 1, the fluid injector system 100 includes an injector housing 102 having opposed lateral sides 104, a distal or upper end 106, and a proximal or lower end 108. In some examples, the housing 102 may be supported on a base 110 having one or more wheels 112 for rotatable and movable support of the housing 102 on a floor surface. The one or more wheels 112 may be lockable to prevent the housing 102 from inadvertently moving once positioned at a desired location. At least one handle 114 may be provided to facilitate moving and positioning the fluid injector system 100. In other examples, the housing 102 may be removably or non-removably secured to a fixed surface, such as a floor, ceiling, wall, or other structure. The housing 102 encloses the various mechanical drive components, electrical and power components necessary to drive the mechanical drive components, and control components, such as electronic memory and electronic control devices (hereinafter electronic control device(s)), used to control operation of reciprocally movable piston elements 103 (shown in FIG. 2) associated with the fluid injector system 100 described herein. Such piston elements 103 may be reciprocally operable via electro-mechanical drive components such as a ball screw shaft driven by a motor, a voice coil actuator, a rack-and-pinion gear drive, a linear motor, and the like. In some examples, at least some of the mechanical drive components, electrical and power components, and control components may be provided on the base 110.

With continued reference to FIG. 1, the fluid injector system 100 has at least one door 116 that encloses at least some of the MUDS, the mechanical drive components, electrical and power components, and control components. The door 116 is desirably movable between an open position and a closed position (shown in FIG. 1). In some examples, the door 116 may be lockable.

The fluid injector system 100 further includes at least one bulk fluid connector 118 for connection with at least one bulk fluid source 120. In some examples, a plurality of bulk fluid connectors 118 may be provided. For example, as shown in FIG. 1, three bulk fluid connectors 118 may be provided in a side-by-side or other arrangement. In some examples, the at least one bulk fluid connector 118 may be a spike configured for removably connecting to the at least one bulk fluid source 120, such as a vial, a bottle, or a bag. The at least one bulk fluid connector 118 may have a reusable or non-reusable interface with each new bulk fluid source 120. The at least one bulk fluid connector 118 may be formed on the multi-patient disposable set, as described herein. The at least one bulk fluid source 120 may be configured for receiving a medical fluid, such as saline, contrast solution, or other medical fluid, for delivery to the fluid injector system 100. The housing 102 may have at least one support member 122 for supporting the at least one bulk fluid source 120 once it is connected to the fluid injector system 100.

With continued reference to FIG. 1, the fluid injector system 100 includes one or more user interfaces 124, such as a graphical user interface (GUI) display window. The user interface 124 may display information pertinent to a fluid injection procedure involving fluid injector system 100, such as current flow rate, fluid pressure, and volume remaining in the at least one bulk fluid source 120 connected to the fluid injector system 100 and may be a touch screen GUI that allows an operator to input commands and/or data for operation of fluid injector system 100. While the user interface 124 is shown on the injector housing 102, such user interface 124 may also be in the form of a remote display that is wired or wirelessly linked to the housing 102 and control and mechanical elements of fluid injector system 100. In some examples, the user interface 124 may be a tablet computer that is detachably connected to the housing 102 and is in wired or wirelessly linked communication with the housing 102. Additionally, the fluid injector system 100 and/or user interface 124 may include at least one control button 126 for tactile operation by an attendant operator of the fluid injector system 100. In certain examples, the at least one control button 126 may be part of a keyboard for inputting commands and/or data by the operator. The at least one control button 126 may be hard-wired to the electronic control device(s) associated with the fluid injector system 100 to provide direct input to the electronic control device(s). The at least one control button 126 may also be a graphical part of the user interface 124, such as a touch screen. In either arrangement, the at least one control button 126 desirably provides certain individual control features to the attendant operator of the fluid injector system 100, such as, but not limited to: (1) acknowledging that a multi-patient disposable set has been loaded or unloaded; (2) locking/unlocking of the multi-patient disposable set; (3) filling/purging of the fluid injector system 100; (4) inputting information and/or data related to the patient and/or injection procedure; and (5) initiating/stopping an injection procedure. The user interface 124 and/or any electronic processing units associated with the fluid injector system 100 may be wired or wirelessly connected to an operation and/or data storage system such as a hospital network system.

Figure 2:
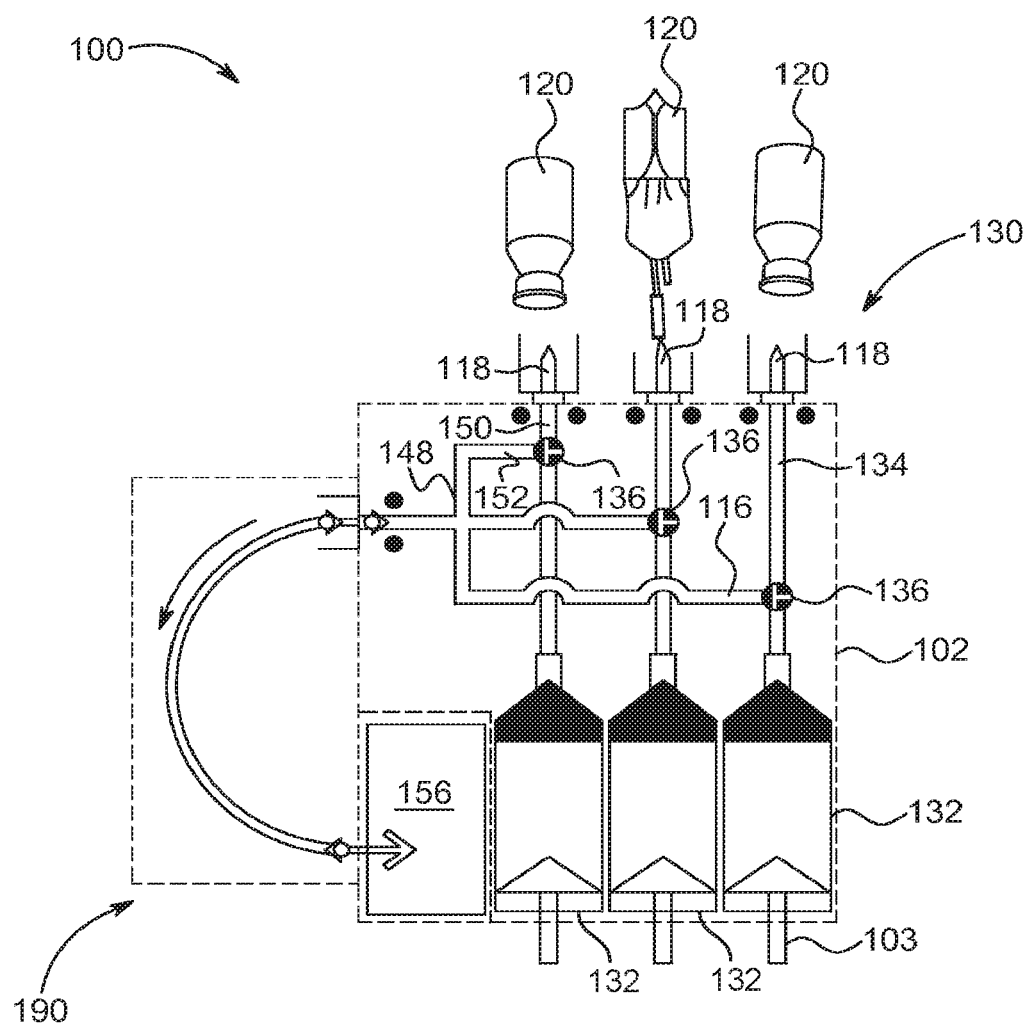
FIG. 2 is schematic view of various fluid paths within the multi-fluid delivery system of FIG. 1.

With reference to FIG. 2, the fluid injector system 100 includes a MUDS 130 that is removably connected to the fluid injector system 100 for delivering one or more fluids from the one or more bulk fluid sources 120 to the patient. Examples and features of the MUDS are further described in International Application No. WO 2016/112163, filed on Jan. 7, 2016 and entitled "Multiple Fluid Delivery System with Multi-Use Disposable Set and Features Thereof", the disclosure of which is incorporated herein by reference in its entirety. The MUDS 130 may include one or more syringes or pumps 132. In some examples, the number of syringes 132 may correspond to the number of bulk fluid sources 120. For example, with reference to FIG. 2, the MUDS 130 has three syringes 132 in a side-by-side arrangement such that each syringe 132 is fluidly connectable to one or more of the bulk fluid sources 120. In some examples, one or two bulk fluid sources 120 may be connected to one or more syringes 132 of the MUDS 130. Each syringe 132 may be fluidly connectable to one of the bulk fluid sources 120 by a corresponding bulk fluid connector 118 and an associated MUDS fluid path 134. The MUDS fluid path 134 may have a spike element that connects to the bulk fluid connector 118. In some examples, the bulk fluid connector 118 may be provided directly on the MUDS 130.

With further reference to FIG. 2, the MUDS 130 is removably connectable to the housing 102 of the fluid injector system 100. As will be appreciated by one having ordinary skill in the art, it may be desirable to construct at least a portion of the MUDS 130 from a clear medical grade plastic in order to facilitate visual verification that a fluid connection has been established with the fluid injector system 100. Visual verification is also desirable for confirming that no air bubbles are present within various fluid connections. Alternatively, at least a portion of the MUDS 130 and/or door 116 may include windows (not shown) for visualization of the connection between various components. Various optical sensors (not shown) may also be provided to detect and verify the connections. Additionally, various lighting elements (not shown), such as light emitting diodes (LEDs), may be provided to actuate one or more optical sensors and indicate that a suitable connection has been established between the various components.

With specific reference to FIG. 2, a schematic view of various fluid paths of the fluid injector system 100 is provided. The MUDS 130 may include one or more valves 136, such as stopcock valves, for controlling which medical fluid or combinations of medical fluids are withdrawn from the multi-dose bulk fluid source 120 and/or are delivered to a patient through each syringe 132. In some examples, the one or more valves 136 may be provided on a distal end of the plurality of syringes 132 or on a manifold 148. The manifold 148 may be in fluid communication via valves 136 and/or syringes 132 with a first end of the MUDS fluid path 134 that connects each syringe 132 to the corresponding bulk fluid source 120. The opposing second end of the MUDS fluid path 134 may be connected to the respective bulk fluid connector 118 that is configured for fluidly connecting with the bulk fluid source 120. Depending on the position of the one or more valves 136, fluid may be drawn into the one or more syringes 132 or it may be delivered from the one or more syringes 132. In a first position, such as during the filling of the syringes 132, the one or more valves 136 are oriented such that fluid flows from the bulk fluid source 120 into the desired syringe 132 through a fluid inlet line 150, such as a MUDS fluid path. During the filling procedure, the one or more valves 136 are positioned such that fluid flow through one or more fluid outlet lines 152 or manifold 148 is blocked. In a second position, such as during a fluid delivery procedure, fluid from one or more syringes 132 is delivered to the manifold 148 through the one or more fluid outlet lines 152 or syringe valve outlet ports. During the delivery procedure, the one or more valves 136 are positioned such that fluid flow through one or more fluid inlet lines 150 is blocked. The one or more valves 136, fluid inlet lines 150, and/or fluid outlet lines 152 may be integrated into the manifold 148. The one or more valves 136 may be selectively positioned to the first or second position by manual or automatic handling. For example, the operator may position the one or more valves 136 into the desired position for filling or fluid delivery. In other examples, at least a portion of the fluid injector system 100 is operable for automatically positioning the one or more valves 136 into a desired position for filling or fluid delivery based on input by the operator, as described herein.

With continued reference to FIG. 2, in some examples, the fluid outlet line 152 may also be connected to a waste reservoir 156 on the fluid injector system 100. The waste reservoir 156 is desirably separate from the syringes 132 to prevent contamination. In some examples, the waste reservoir 156 is configured to receive waste fluid expelled from the syringes 132 during, for example, a priming operation. The waste reservoir 156 may be removable from the housing 102 in order to dispose of the contents of the waste reservoir 156. In other examples, the waste reservoir 156 may have a draining port (not shown) for emptying the contents of the waste reservoir 156 without removing the waste reservoir 156 from the housing 102. In some examples, the waste reservoir 156 is provided as a separate component from the MUDS 130.

Having generally described the components of the fluid injector system 100 and the MUDS 130, the structure and method of use of a single-use disposable set 190 (SUDS) and its interaction with MUDS 130 will now be described.

Figure 3A:
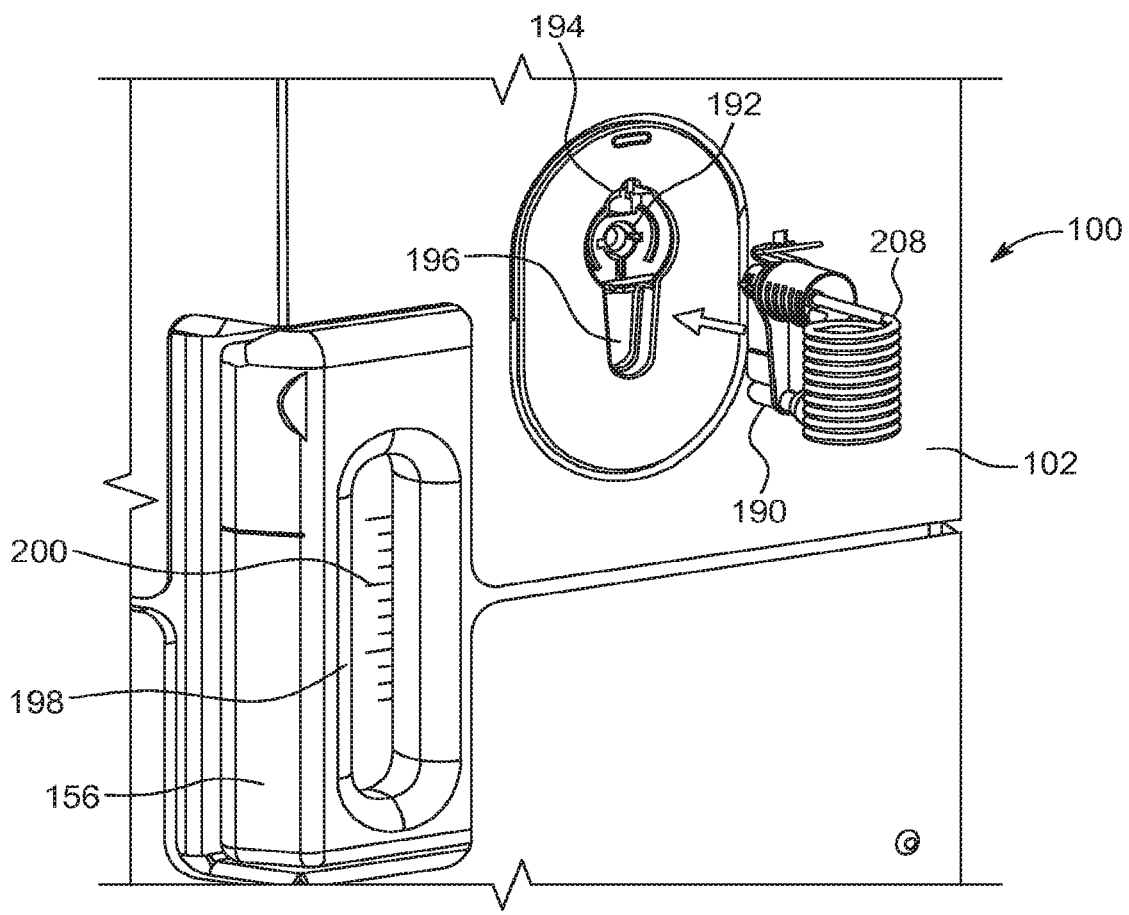
FIG. 3A is a perspective view of a connection interface prior to connecting a single-use disposable set connector with a multi-fluid delivery system.
Figure 3B:
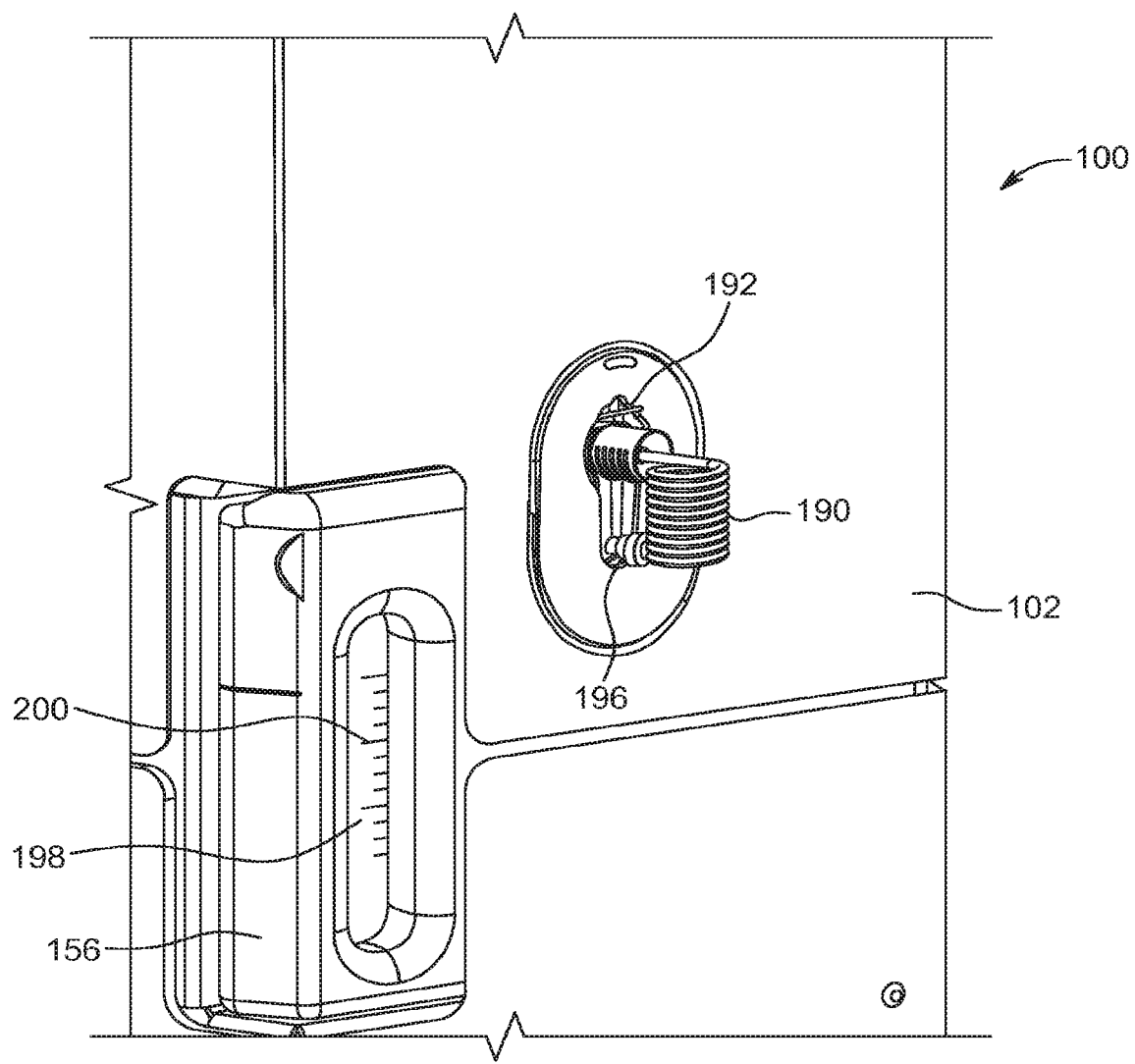
FIG. 3B is a perspective view of the connection interface of FIG. 3A showing the single-use disposable set connector connected with the multi-fluid delivery system.

With reference to FIGS. 3A and 3B, the fluid injector system 100 has a connection port 192 that is configured to form a releasable fluid connection with at least a portion of the SUDS 190. In some examples, the connection port 192 may be formed on the MUDS 130. The connection port 192 may be shielded by at least a portion of the housing 102 of the fluid injector system 100. For example, recessing the connection port 192 within the interior of the housing 102 may preserve the sterility of the connection port 192 by preventing or limiting a user or patient from touching and contaminating the portions of the connection port 192 that contact the fluid to be injected to the patient. In some examples, the connection port 192 is recessed within an opening 194 formed on the housing 102 of the fluid injector system 100, or the connection port 192 may have a shielding structure (not shown) that surrounds at least a portion of the connection port 192. In other examples, the connection port 192 may be formed directly on the housing 102 and connected to the MUDS 130 by a fluid path (not shown). As described herein, the SUDS 190 may be connected to the connection port 192, formed on at least a portion of the MUDS 130 and/or the housing 102. Desirably, the connection between the SUDS 190 and the connection port 192 is a releasable connection to allow the SUDS 190 to be selectively disconnected from the connection port 192 (FIG. 3A) and connected to the connection port 192 (FIG. 3B). In some examples, the SUDS 190 may be disconnected from the connection port 192 and disposed after each fluid delivery procedure, and a new SUDS 190 may be connected to the connection port 192 for a subsequent fluid delivery procedure.

With continued reference to FIGS. 3A and 3B, a waste inlet port 196 may be provided separately from the connection port 192. The waste inlet port 196 is in fluid communication with the waste reservoir 156. In some examples, the waste reservoir 156 is provided separately from the SUDS 190 such that the fluid from the waste inlet port 196 can be delivered to the waste reservoir 156. At least a portion of the SUDS 190 may be releasably connected to or associated with the waste inlet port 196 for introducing waste fluid into the waste reservoir 156 during, for example, a priming operation that expels air from the SUDS 190. The waste reservoir 156 may have a viewing window 198 with indicia 200, such as graduated markings, that indicate the fill level of the waste reservoir 156.

Figure 4A:
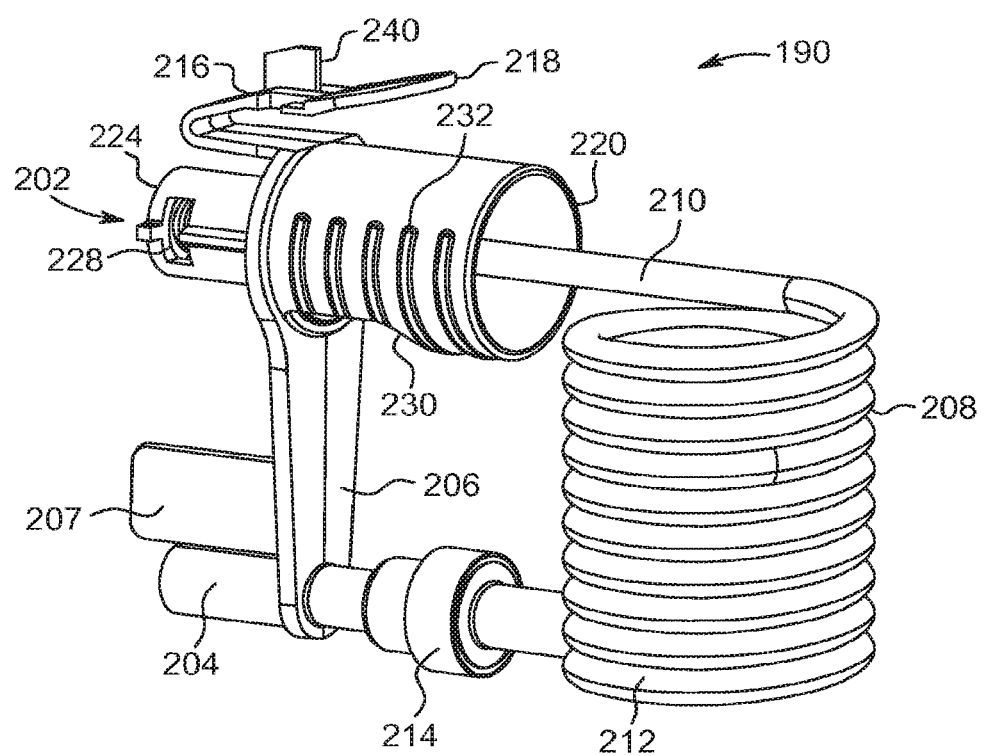
FIG. 4A is a perspective view of a single-use disposable set connector in accordance with one example.
Figure 4B:
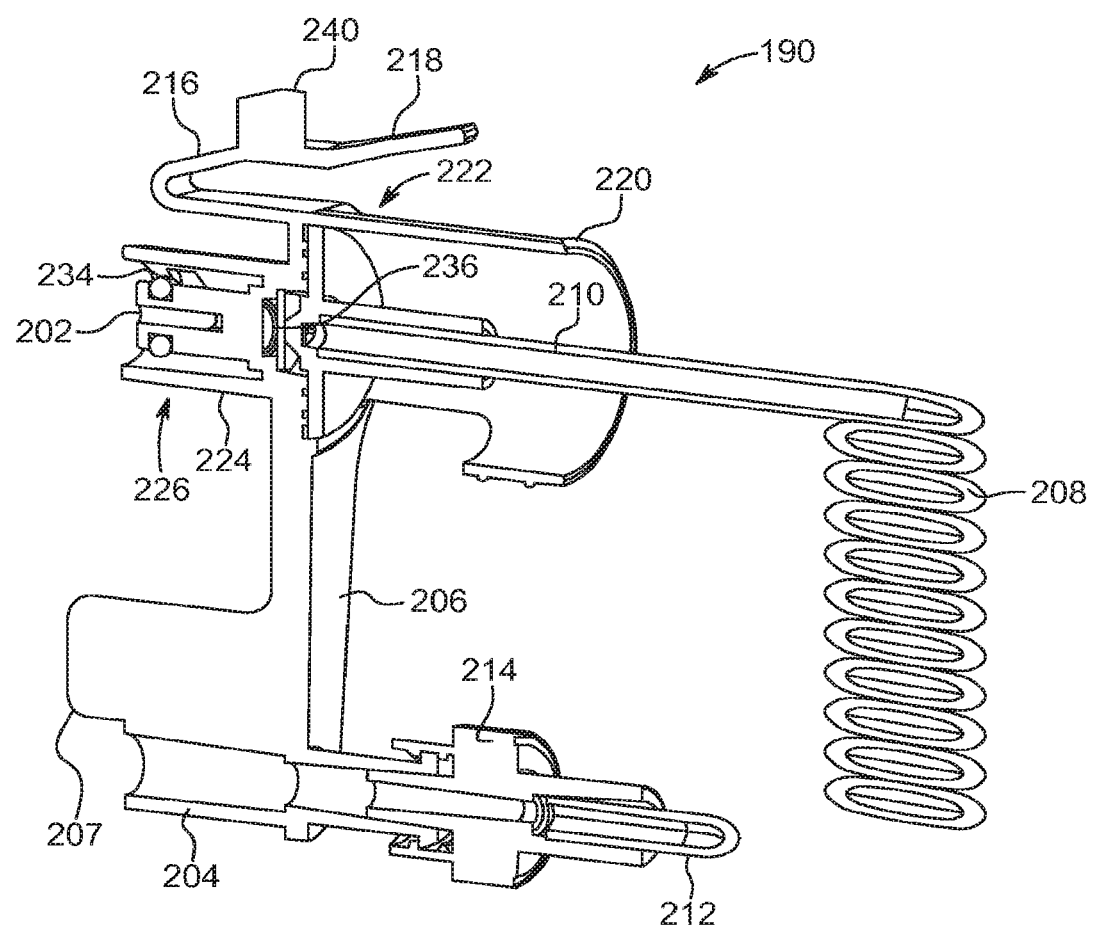
FIG. 4B is a cross-sectional view of the single-use disposable set connector shown in FIG. 4A.

With reference to FIG. 4A, the SUDS 190 has a fluid inlet port 202 that is configured for releasable connection with the connection port 192 (shown in FIG. 3A). The fluid inlet port 202 receives fluid delivered from the fluid injector system 100. The fluid inlet port 202 is desirably a hollow, tubular structure, as shown in FIG. 4B. The SUDS 190 further has a waste outlet port 204 that is configured for releasable connection or association with the waste inlet port 196 (shown in FIG. 3A). The waste outlet port 204 receives waste fluid and delivers such waste fluid to the waste reservoir 156 during, for example, a priming operation of the SUDS 190. The waste outlet port 204 is desirably a hollow, tubular structure, as shown in FIG. 4B. The waste outlet port 204 may be connected to, inserted into, or located in the waste inlet port 202 so that the waste fluid may flow through the waste inlet port 202 and continue into waste reservoir 156. The fluid inlet port 202 and the waste outlet port 204 may be spaced apart from each other by a spacer 206. In some examples, the spacer 206 is dimensioned to position the fluid inlet port 202 and the waste outlet port 204 for alignment with the connection port 192 and the waste inlet port 196, respectively. It is noted that the SUDS 190 is shown in FIG. 4A in a state after removal from packaging (not shown). Prior to use, the SUDS 190 is desirably packaged in a pre-sterilized, sealed package that protects the SUDS 190 from contamination with airborne or surface-borne contaminants. Alternatively, the sealed package and the SUDS 190 may be sterilized after packaging.

The SUDS 190 desirably has an asymmetrical structure, so that the user can only attach the SUDS 190 to the MUDS 130 in one orientation. In this manner, the user is prevented from attaching the fluid inlet port 202 to the waste inlet port 196. In some examples, a fin 207 may be provided on at least a portion of the SUDS 190 to prevent erroneous insertion of the SUDS 190 in the connection port 192. In certain examples, the fin 207 may be formed on the spacer 206 proximate to the waste outlet port 204. In this manner, the fin 207 may interfere with the incorrect insertion of the SUDS 190 into the connection port 192. Structures and shapes other than fin 207 may be used to prevent erroneous insertion of the SUDS 190 into connection port 192.

Figure 4C:
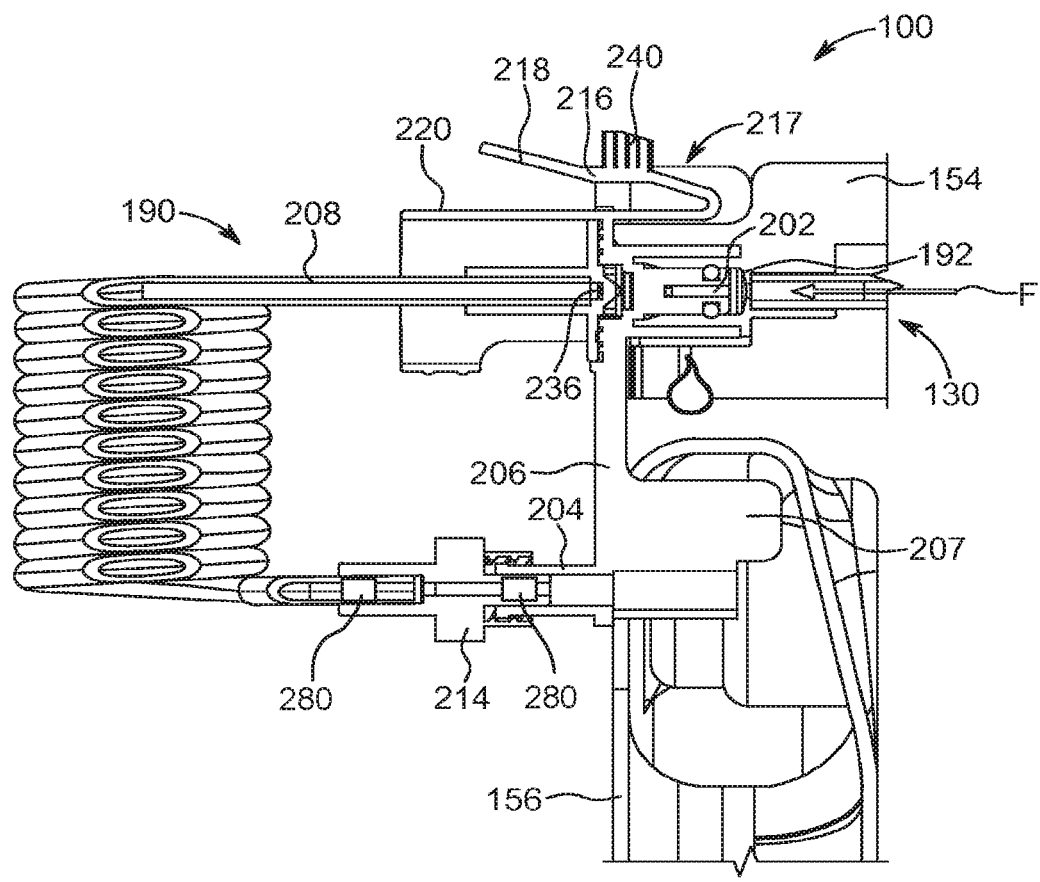
FIG. 4C is a cross-sectional view of the single-use disposable set connector shown in FIG. 4A connected to a port of a multi-fluid delivery system.

In some examples, tubing 208 may be connected at its proximal end 210 to the fluid inlet port 202. The tubing 208 is configured to deliver fluid received from the fluid inlet port 202. The distal end 212 of the tubing 208 may have a connector 214, which may include a one-way check valve, that is configured for connection with the waste outlet port 204 or a fluid path connected to the patient (not shown). The tubing 208 may be made from a flexible material, such as a medical grade plastic material, that allows the tubing 208 to be coiled. The connector 214 may be a luer-lock connector (either a male luer-lock connector or a female luer-lock connector depending on the desired application) or other medical connector configuration. In some examples, the connector 214 may include at least one one-way check valve 280 therein, as shown in FIG. 4C, to prevent backflow of fluid. Alternatively, a one-way check valve may be located elsewhere in the SUDS 190 between fluid inlet port 202 and connector 214.

With continued reference to FIG. 4A, the SUDS 190 may have a locking tab 216 that is configured for selectively locking the SUDS 190 with the fluid injector system 100 depending on the engagement of the locking tab 216 with at least a portion of the fluid injector system 100. In some examples, the locking tab 216 may be a flexible tab that is deflectable between an engaged position and a disengaged position by deflecting at least a portion of the locking tab 216. The locking tab 216 may have a pressing surface 218 that, when pressed, causes the locking tab 216 to be deflected from the engaged position to the disengaged position for insertion and removal of the SUDS 190 from the fluid injector system 100. In some examples, the locking tab 216 may be configured for releasable locking engagement with a receiving slot 217 on the MUDS 130 (shown in FIG. 4C).

With reference to FIG. 4B, the SUDS 190 may have a first annular skirt 224 extending circumferentially around a proximal end 226 of the fluid inlet port 202 and a second annular skirt 220 extending circumferentially around a distal end 222 of the fluid inlet port 202. The first and second annular skirts 224, 220 surround the fluid inlet port 202 to prevent inadvertent contact and contamination. The first annular skirt 224 may have one or more recesses 228 (shown in FIG. 4A) extending through a sidewall thereof. The one or more recesses 228 may provide a locking interface with a corresponding locking element (not shown) on the fluid injector system 100. The second annular skirt 220 may have at least one indentation 230 (shown in FIG. 4A) to facilitate grasping and handling of the SUDS 190. In some examples, the second annular skirt 220 may have a textured surface having one or more ribs to facilitate gripping and handling of the SUDS 190.

With continued reference to FIG. 4B, at least one annular seal 234 may be provided around the proximal end 226 of the fluid inlet port 202. The at least one annular seal 234 may seal the fluid inlet port 202 to prevent fluid from leaking through the SUDS 190. The at least one annular seal 234 may provide a fluid seal between the SUDS 190 and the MUDS 130 when they are fluidly connected with one another to allow fluid to flow from the MUDS 130 to the SUDS 190 without leaking. A one-way check valve 236 may be provided within a lumen of the fluid inlet port 202 to prevent fluid from flowing in a reverse direction from the SUDS 190 into the MUDS 130.

With reference to FIG. 4C, the SUDS 190 shown in FIG. 4A is shown connected to the fluid injector system 100. While FIG. 4C illustrates the connection port 192 formed on the MUDS 130, in other examples, the connection port 192 may be formed on a portion of the housing 102 (shown in FIG. 1). The fluid inlet port 202 of the SUDS 190 is connected to the connection port 192 to establish a fluid path in a direction of arrow F shown in FIG. 4C. Fluid passing through the fluid inlet port 202 flows through the one-way valve 236 and into tubing 208. Any fluid that may drip from the interface between the fluid inlet port 202 and the connection port 192 is collected in the waste reservoir 156. The waste reservoir 156 may be shaped to collect any fluid that may drip from the SUDS 190 when it is removed from the MUDS 130. Additionally, when the SUDS 190 is connected to the connection port 192, the outlet of the waste outlet port 204 is positioned within the waste inlet port 196 such that waste fluid from the tubing 208 may be discharged into the waste reservoir 156. The spacer 206 may define an insertion stop surface to define the depth of insertion of the SUDS 190 into the connection port 192.

Figure 5:
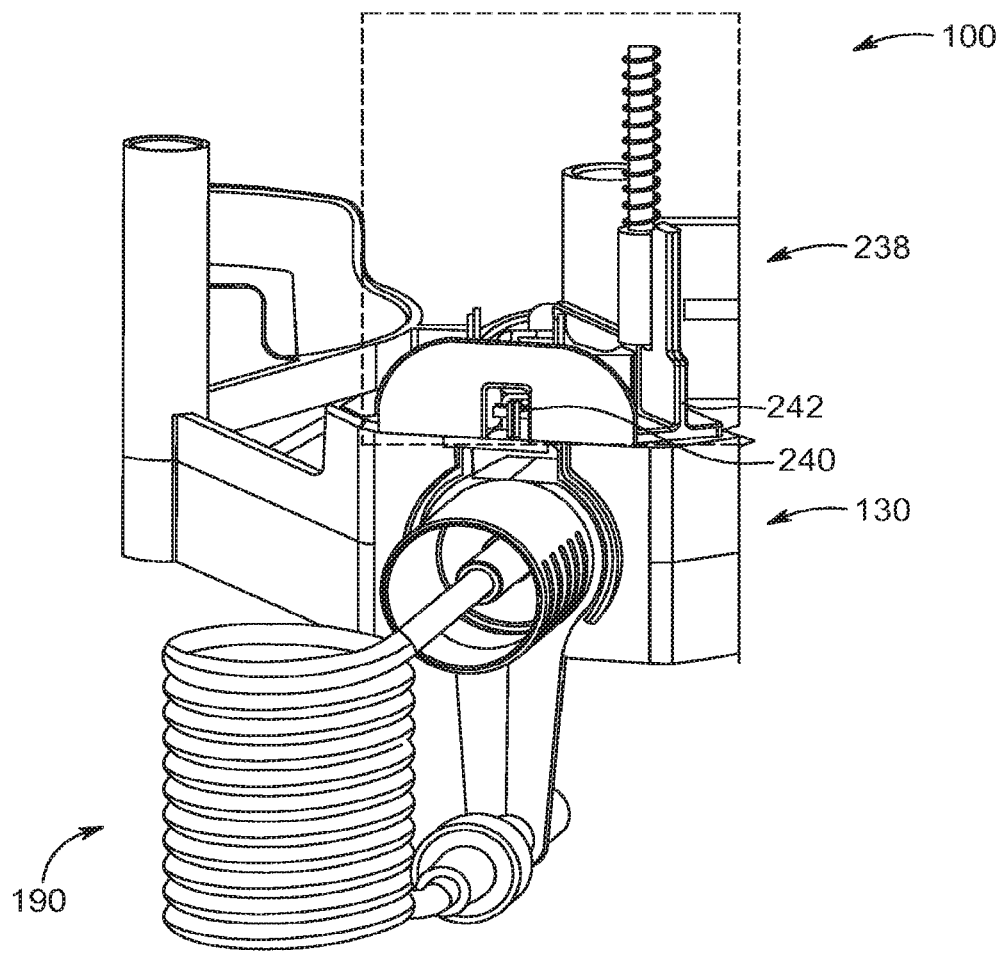
FIG. 5 is a perspective view of the single-use disposable set connector shown in FIG. 4C with a portion of the multi-fluid delivery system and the multi-patient disposable set cutaway.

With reference to FIG. 5, the fluid injector system 100 may have a sensor system 238 adapted to identify when the SUDS 190 is in fluid communication with the MUDS 130. The sensor system 238 may include at least one sensing element, such as a sensor fin 240, on the SUDS 190 and a corresponding sensor 242 on the fluid injector system 100 or MUDS 130. The sensor 242 may be configured to detect the presence and absence of the at least one sensor fin 240 or other sensing element. In some examples, the sensing element, such as the at least one sensor fin 240, is formed on the locking tab 216 of the SUDS 190, such as shown in FIG. 4A. In other examples, the sensing element, such as the at least one sensor fin 240, may be formed on any portion of the SUDS 190. The sensor 242 may be an optical sensor that is seated and secured within a respective mount formed on the housing 102 of the fluid injector system 100. As will be appreciated by those versed in the field of powered medical fluid injectors, the sensor 242 may be electronically coupled to an electronic control device used to discretely control operation of the fluid injector system, such as the operation of the one or more piston elements, based, at least in part, on input from the sensor 242. The sensing element, such as the sensor fin 240 may have one or more reflective surfaces that reflect visible or infrared light to be detected by the sensor 242. In other examples, mechanical interaction between the sensing element and the sensor 242 may be used.

In some examples, the SUDS 190 may further include reuse prevention features. For example, the SUDS 190 may include one or more breakable sensor elements, tabs, or structures that fold or break when the SUDS 190 is removed from the MUDS 130. Absence of these features may prevent reinsertion and reuse of the SUDS 190 after removal. In this manner, it can be assured that the SUDS 190 is only used for one fluid delivery procedure.

Other examples and features of the SUDS 190 are described in U.S. Patent Publication No. 2016/0331951, filed Jul. 7, 2016 and entitled "Single-Use Disposable Set Connector", the disclosure of which is incorporated herein by reference in its entirety.

Having generally described the components of the fluid injector system 100, the MUDS 130, and the SUDS 190, a method of operation of using the SUDS 190 will now be described in detail. In use, a medical technician or user removes the disposable SUDS 190 from its packaging (not shown) and inserts the fluid inlet port 202 into the connection port 192 on the MUDS 130. As described above, the SUDS 190 must be inserted in the correct orientation such that the fluid inlet port 202 is aligned for connection with the connection port 192 and the waste outlet port 204 is aligned for connection with the waste inlet port 196. The SUDS 190 may be secured to the MUDS 130 by inserting the locking tab 216 into the receiving slot 217 on the MUDS 130. Once the SUDS 190 is securely connected to the MUDS 130, for example as sensed by the sensor 242, the fluid injector system 100 (shown in FIG. 1) draws fluid into one or more of the plurality of syringes 132 of the MUDS 130 and performs an automatic priming operation for removing air from the MUDS 130 and the SUDS 190. During such priming operation, fluid from the MUDS 130 is injected through the connection port 192 and into the tubing 208 of the SUDS 190. The fluid flows through the tubing 208, the connector 214 and through the waste outlet port 204 and into the waste reservoir 156. Once the automatic priming operation is completed, the medical technician disconnects the connector 214 from the waste outlet port 204. The connector 214 may then be connected to the patient through a catheter, vascular access device, needle, or additional fluid path set to facilitate fluid delivery to the patient. Once the fluid delivery is completed, the SUDS 190 is disconnected from the patient and the MUDS 130 by disengaging the locking tab 216 of the SUDS 190 from the receiving slot 217 on the MUDS 130. The medical technician may then dispose of the SUDS 190. In certain examples, removing the SUDS 190 from the MUDS 130 causes reuse prevention features (not shown) to activate, thereby preventing reinsertion and reuse of the SUDS 190.

Figure 6:
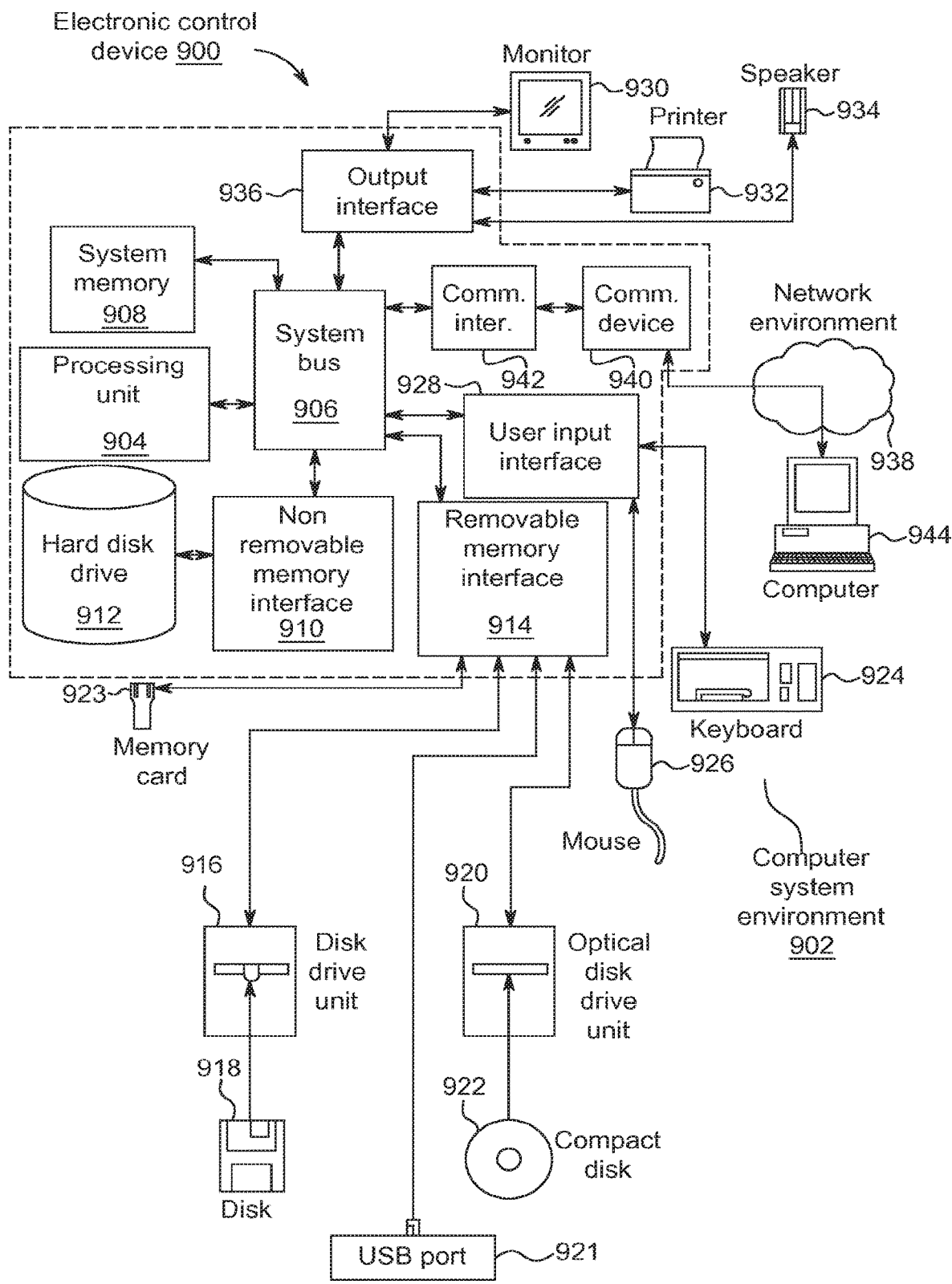
FIG. 6 is a schematic view of an electronic control system of a multi-fluid injection system in accordance with another example.

With reference to FIG. 6, an electronic control device 900 may be associated with fluid injector system 100 to control the filling and delivery operations. In some examples, the electronic control device 900 may control the operation of various valves, piston members, and other elements to effect a desired filling or delivery procedure. For example, the electronic control device 900 may include a variety of discrete computer-readable media components. For example, this computer-readable media may include any media that can be accessed by the electronic control device 900, such as volatile media, non-volatile media, removable media, non-removable media, transitory media, non-transitory media, etc. As a further example, this computer-readable media may include computer storage media, such as media implemented in any method or technology for storage of information, such as computer-readable instructions, data structures, program modules, or other data; random access memory (RAM), read-only memory (ROM), electrically erasable programmable read-only memory (EEPROM), flash memory, or other memory technology; CD-ROM, digital versatile disks (DVDs), or other optical disk storage; magnetic cassettes, magnetic tape, magnetic disk storage, or other magnetic storage devices; or any other medium which can be used to store the desired information and which can be accessed by the electronic control device 900. Further, this computer-readable media may include communications media, such as computer-readable instructions, data structures, program modules, or other data in a modulated data signal, such as a carrier wave or other transport mechanism and include any information delivery media, wired media (such as a wired network and a direct-wired connection), and wireless media (such as acoustic signals, radio frequency signals, optical signals, infrared signals, biometric signals, bar code signals, etc.). Of course, combinations of any of the above should also be included within the scope of computer-readable media.

The electronic control device 900 further includes a system memory 908 with computer storage media in the form of volatile and non-volatile memory, such as ROM and RAM. A basic input/output system (BIOS) with appropriate computer-based routines assists in transferring information between components within the electronic control device 900 and is normally stored in ROM. The RAM portion of the system memory 908 typically contains data and program modules that are immediately accessible to or presently being operated on by a processing unit 904, e.g., an operating system, application programming interfaces, application programs, program modules, program data, and other instruction-based computer-readable codes.

With continued reference to FIG. 6, the electronic control device 900 may also include other removable or non-removable, volatile or non-volatile, transitory or non-transitory computer storage media products. For example, the electronic control device 900 may include a non-removable memory interface 910 that communicates with and controls a hard disk drive 912, e.g., a non-removable, non-volatile magnetic medium; and a removable, non-volatile memory interface 914 that communicates with and controls a magnetic disk drive unit 916 (which reads from and writes to a removable, non-volatile magnetic disk 918), an optical disk drive unit 920 (which reads from and writes to a removable, non-volatile optical disk 922, such as a CD ROM), a Universal Serial Bus (USB) port 921 for use in connection with a removable memory card, etc. However, it is envisioned that other removable or non-removable, volatile or non-volatile computer storage media can be used in an exemplary computing system environment 902, including, but not limited to, magnetic tape cassettes, DVDs, digital video tape, solid state RAM, solid state ROM, etc. These various removable or non-removable, volatile or non-volatile magnetic media are in communication with the processing unit 904 and other components of the electronic control device 900 via a system bus 906. The drives and their associated computer storage media, discussed above and illustrated in FIG. 6, provide storage of operating systems, computer-readable instructions, application programs, data structures, program modules, program data, and other instruction-based, computer-readable code for the electronic control device 900 (whether duplicative or not of this information and data in the system memory 908).

A user may enter commands, information, and data into the electronic control device 900 through certain attachable or operable input devices, such as the user interface 124 shown in FIG. 1, via a user input interface 928. A variety of such input devices may be utilized, e.g., a microphone, a trackball, a joystick, a touchpad, a touch-screen, a scanner, etc., including any arrangement that facilitates the input of data and information to the electronic control device 900 from an outside source. As discussed, these and other input devices are often connected to the processing unit 904 through the user input interface 928 coupled to the system bus 906, but may be connected by other interface and bus structures, such as a parallel port, game port, or a USB. Still further, data and information can be presented or provided to a user in an intelligible form or format through certain output devices, such as a monitor 930 (to visually display this information and data in electronic form), a printer 932 (to physically display this information and data in print form), a speaker 934 (to audibly present this information and data in audible form), etc. All of these devices are in communication with the electronic control device 900 through an output interface 936 coupled to the system bus 906. It is envisioned that any such peripheral output devices be used to provide information and data to the user.

The electronic control device 900 may operate in a network environment 938 through the use of a communications device 940, which is integral to the electronic control device 900 or remote therefrom. This communications device 940 is operable by and in communication with the other components of the electronic control device 900 through a communications interface 942. Using such an arrangement, the electronic control device 900 may connect with or otherwise communicate with one or more remote computers, such as a remote computer 944, which may be a personal computer, a server, a router, a network personal computer, a peer device, or other common network nodes, and typically includes many or all of the components described above in connection with the electronic control device 900. Using appropriate communication devices 940, e.g., a modem, a network interface or adapter, etc., the computer 944 may operate within and communicate through a local area network (LAN) and a wide area network (WAN), but may also include other networks such as a virtual private network (VPN), an office network, an enterprise network, an intranet, the Internet, etc.

As used herein, the electronic control device 900 includes or is operable to execute appropriate custom-designed or conventional software to perform and implement the processing steps of the method and system of the present disclosure, thereby forming a specialized and particular computing system. Accordingly, the method and system may include one or more electronic control devices 900 or similar computing devices having a computer-readable storage medium capable of storing computer-readable program code or instructions that cause the processing unit 904 to execute, configure, or otherwise implement the methods, processes, and transformational data manipulations discussed hereinafter in connection with the present disclosure. Still further, the electronic control device 900 may be in the form of a personal computer, a personal digital assistant, a portable computer, a laptop, a palmtop, a mobile device, a mobile telephone, a server, or any other type of computing device having the necessary processing hardware to appropriately process data to effectively implement the computer-implemented method and system.

It will be apparent to one skilled in the relevant arts that the system may utilize databases physically located on one or more computers which may or may not be the same as their respective servers. For example, programming software on electronic control device 900 can control a database physically stored on a separate processor of the network or otherwise.

In some examples, the electronic control device 900 may be programmed so that automatic refill occurs based upon a preprogrammed trigger minimum volume in the respective syringes 132. For example, when the volume of fluid remaining in at least one of the syringes 132 is less than a programmed volume, a syringe refill procedure is automatically initiated by the electronic control device 900. The electronic control device 900 associated with the fluid injector system 100 may determine that the preprogrammed trigger minimum volume has been reached by tracking the fluid volume dispensed from the respective syringes 132 during operation of the fluid injector system 100. Alternatively, fluid level sensors may be incorporated into the fluid injector system 100 and inputs from these fluid level sensors may be provided to the electronic control device 900 so that the electronic control device 900 may determine when the preprogrammed trigger minimum volume has been reached in at least one of the syringes 132. The fill volume and rate of refill can be preprogrammed in the electronic control device 900. The automatic refill procedure can be stopped either automatically by the electronic control device 900 or may be manually interrupted. In addition, an automatic refill procedure may be initiated when, at the completion of a fluid injection procedure, there is not enough fluid in at least one of the syringes 132 to perform the next programmed fluid injection procedure.

During a refill procedure it is possible that one or more of the bulk fluid sources 120 associated with the respective syringes 132 may become empty (e.g., initially lack sufficient fluid to complete a full refill of the one or more syringes 132). A replacement bulk fluid source 120 is, therefore, necessary and replacement of such bulk fluid source 120 is desirably made quickly. The fluid injector system 100 may have an indicator, such as an audible and/or visual indicator, to indicate to the operator that a change of the bulk fluid source 120 is necessary before the fluid injector system 100 may be used.

As described above, the fluid injector system 100 may automatically prime the MUDS 130 and the SUDS 190 once the SUDS 190 is securely connected to the MUDS 130, for example, as sensed by the sensor 242. During such priming operation, fluid from the MUDS 130 is injected through the connection port 192, into the tubing 208 of the SUDS 190, and into the waste reservoir 156. Fluid flow toward the waste reservoir 156 purges air from the fluid injector system by forcing any air in the MUDS 130 and the SUDS 190 out the distal end 212 of the tubing 208. In some examples, the tubing 208 may inherently emit a distinct acoustic frequency, such as a whistle, caused by air being expelled out the distal end 212 of the tubing 208 as the air flows through the one-way check valve 236 and/or one-way check valve 280 in the fluid inlet port 202 and the connector 214, respectively. In some examples, the waste outlet port 204 may include molded or otherwise manufactured features designed to emit a distinct acoustic frequency caused by air being expelled out the distal end 212 of the tubing 208. The distinct acoustic frequency may be detected and/or measured to verify that the MUDS 130 and the SUDS 190 is being purged of air during the priming operation. In other examples, the tubing 208 may include one or more whistling elements (not shown) configured to produce a distinct acoustic frequency, such as a whistle, when air is expelled out the distal end 212 of the tubing 208. As used herein the term "whistle" refers to a sonic, infrasonic, or ultrasonic wave which may be within, below, or above the range of human audibility. Cessation of the whistle may indicate that the priming operation has been completed. Because the priming operation is tied to the presence and cessation of the whistle, rather than a predetermined fluid volume or predetermined injection time, it is possible to automatically prime the tubing 208 by simply injecting fluid until the whistle ceases, even if the length of the tubing 208 is not known to the MUDS 130. The SUDS 190, being purged of air, is then suitable for connection to a catheter, vascular access device, needle, or additional fluid path set to facilitate fluid delivery to the patient.

Absence of a whistle, or in some instances a negligible whistle, during the automatic priming operation indicates that no air was present in the system, which further indicates that the SUDS 190 was not replaced since the previous priming operation. As such, the detection of a whistle during the priming operation may be used to recognize and deter multiple uses of a given SUDS 190 and encourage adherence to hygienic work practices.

Figure 7:
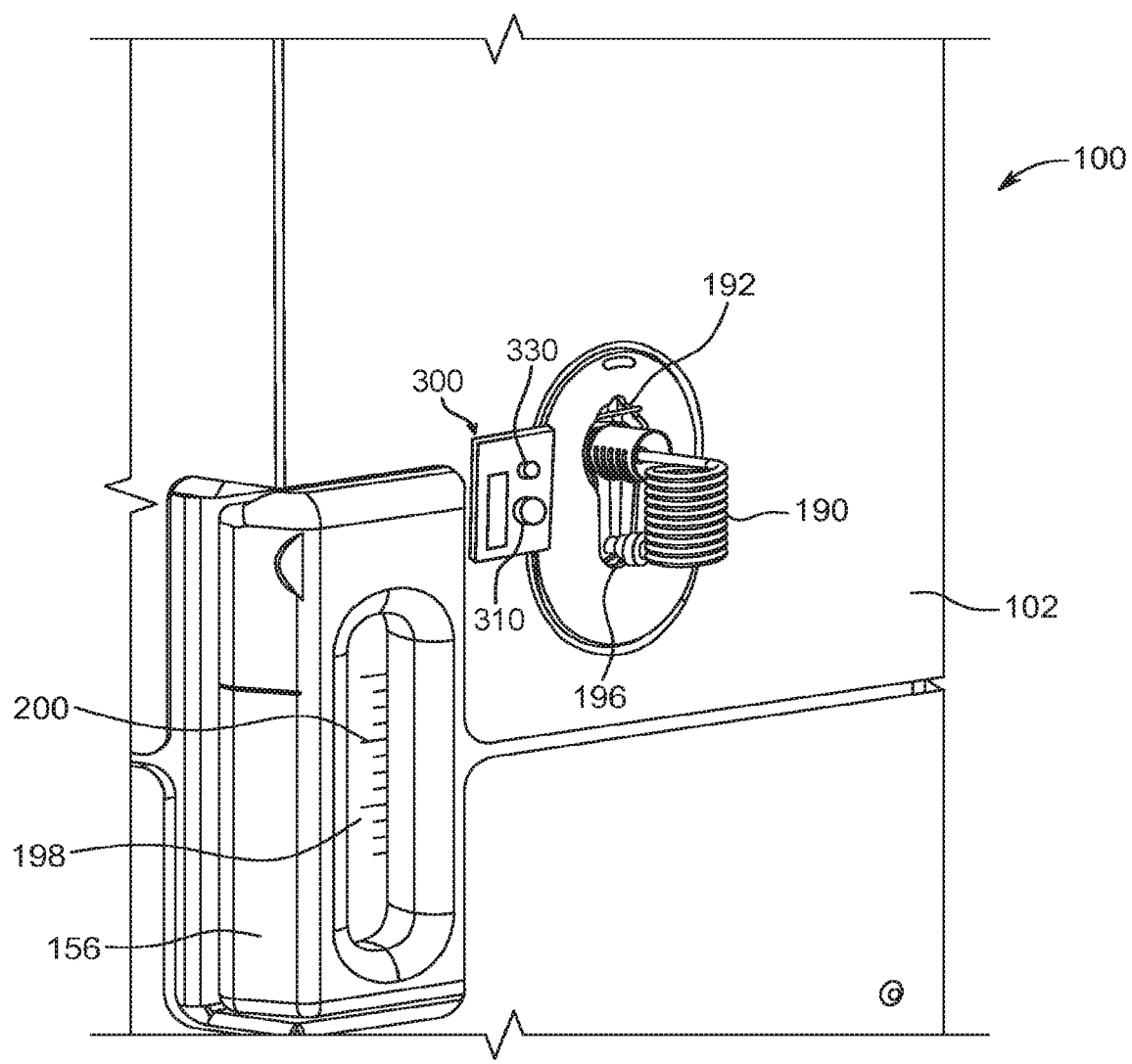
FIG. 7 is a perspective view of the connection interface and single-use disposable set connector of FIG. 3B showing an acoustic frequency detection system according to one example.

Referring now to FIG. 7, the fluid injector system may include an acoustic frequency detection system 300 configured to detect and/or measure the frequency of a sonic, infrasonic, or ultrasonic wave, i.e., a whistle, emitted from the SUDS 190 during the priming operation. The acoustic frequency detection system 300 may include a frequency detector 310, such as a microphone or other device configured to detect sonic, ultrasonic, and/or infrasonic frequency, located in proximity to the one-way check valve 236 and/or the one-way check valve 280 at the distal end 212 of the tubing 208 and configured to emit an electrical signal based on the presence or absence of a whistle from the SUDS 190. That is, the frequency detector 310 may be configured to generate an electrical signal if the sonic, infrasonic, or ultrasonic wave emitted from the one-way check valve 236 and/or the one-way check valve 280 has a frequency within a predetermined range of frequencies corresponding to a frequency of air being expelled from the SUDS 190. Thus, the frequency detector 310 may generate an electrical signal based on the presence of a whistle created by air expelled from SUDS 190. Similarly, the frequency detector 310 may be configured to generate an electrical signal if the sonic, infrasonic, or ultrasonic wave has a frequency outside the predetermined range of frequencies corresponding to the frequency of air being expelled from the SUDS 190.

The acoustic frequency detection system 300 may further include a sensory indicator 330, such as at least one LED or speaker, configured to receive the electrical signal from the frequency detector 310 and provide a visual and/or audible indication of the presence or absence of a whistle from the SUDS 190. For example, the sensory indicator 330 may be at least one LED configured to illuminate a first predetermined color if the frequency detector 310 detects a whistle, indicating that the SUDS 190 has not been previously primed or used. The LED may be configured to illuminate a second predetermined color if the frequency detector 310 does not detect a whistle, indicating that the SUDS 190 has been previously primed and used. In this manner, the acoustic frequency detection system 300 may provide a user with a simple indication that the SUDS 190 has been replaced prior to an instant priming operation. In other examples, the sensory indicator 330 may be a speaker configured to emit a first audible sound if the frequency detector 310 detects a whistle, indicating that the SUDS 190 has not been previously primed or used. The speaker may be configured to emit a second audible sound if the frequency detector 310 does not detect a whistle, indicating that the SUDS 190 has been previously primed and used. In other examples, the sensory indicator 330 may be a combination of at least one LED and at least speaker, each substantially as described above.

In some examples, the acoustic frequency detection system 300 may be incorporated with at least one processor of the electronic control device 900 of the fluid injector system 100 to monitor, record, and/or implement operational changes based upon detection of the frequency of a sonic, infrasonic, or ultrasonic wave emitted from the SUDS 190 during the priming operation. The frequency detector 310 may be configured to generate an electrical signal including frequency data of the sonic, infrasonic, or ultrasonic wave. The frequency data may include the frequency of the sonic, infrasonic, or ultrasonic wave over a duration of the priming operation. The at least one processor of the electronic control device 900 may be configured to receive the electrical signal from the frequency detector 310 and determine, based on the frequency data, whether the frequency of the sonic, infrasonic, or ultrasonic wave emitted from the one-way check valve 236 and/or the one-way check valve 280 at the distal end 212 of the tubing 208 is within a predetermined range of frequencies corresponding to the frequency of air being expelled from the SUDS 190. If the frequency of the sonic, infrasonic, or ultrasonic wave is within a predetermined range of frequencies corresponding to the frequency of air being expelled from the SUDS 190, the at least one processor of the electronic control device 900 may be configured to determine that the SUDS 190 has not been previously primed or used. Conversely, if the frequency of the sonic, infrasonic, or ultrasonic wave is outside a predetermined range of frequencies corresponding to the frequency of air being expelled from the SUDS 190, the at least one processor of the electronic control device 900 may be configured to determine that the SUDS 190 has been previously primed and/or used. Based on the determination of whether the SUDS 190 has been previously primed and/or used, the at least one processor of the electronic control device 900 may be configured to control a subsequent fluid injection operation.

In some examples, the one or more user interfaces 124 of the fluid injector system 100 may display a message based on the determination of whether the SUDS 190 has been previously primed and/or used during the priming operation. In some examples, the electronic control device 900 may be configured to prevent a subsequent fluid injection operation if the at least one processor of the electronic control device 900 determines that the SUDS 190 has been previously primed and/or used. In other examples, the electronic control device 900 may be configured to permit a subsequent fluid injection operation if the at least one processor of the electronic control device 900 determines that the SUDS 190 has not been previously primed and/or used. In this manner, it can be assured that the SUDS 190 is only used for one fluid injection operation.

Figure 8:
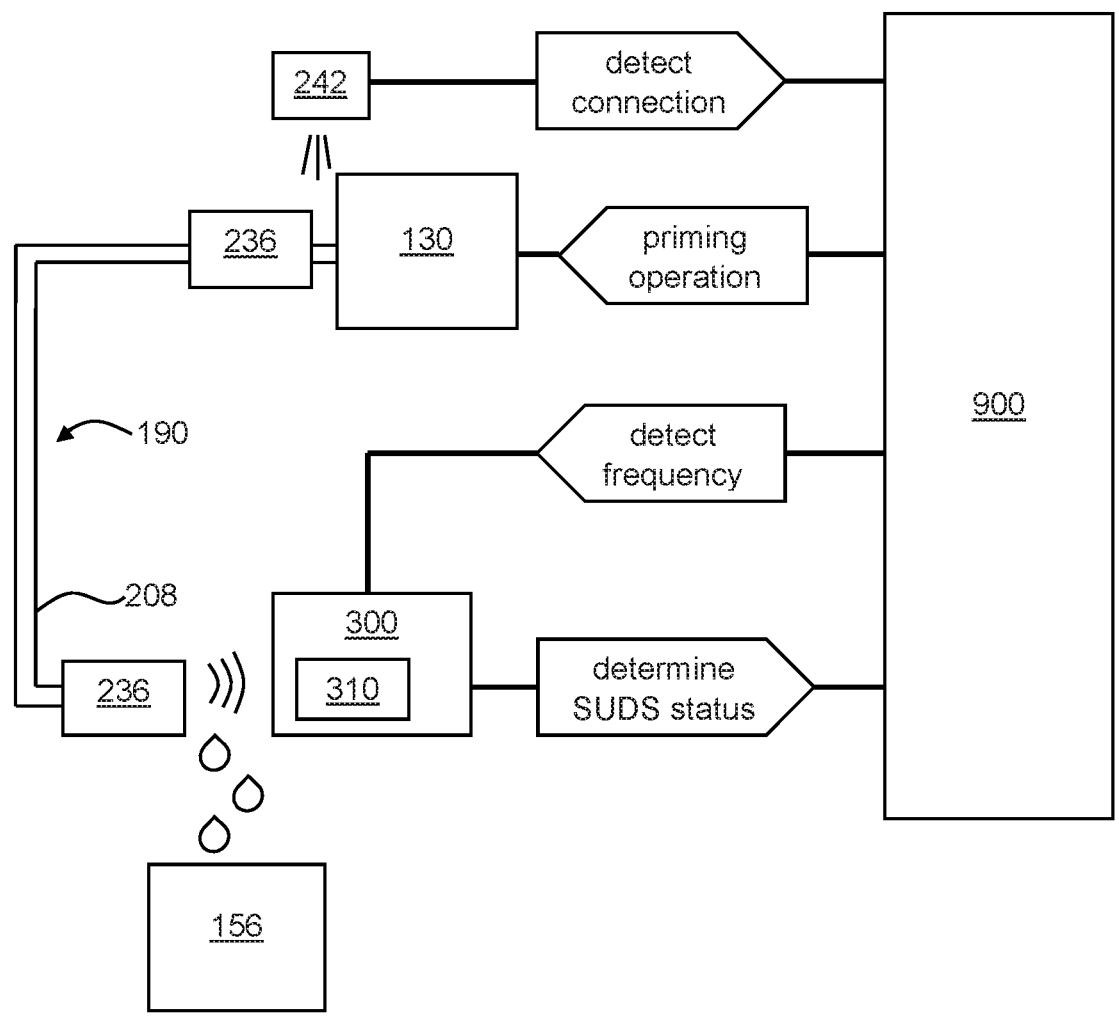
FIG. 8 is a schematic step sequence diagram of the acoustic frequency detection system of FIG. 7.

FIG. 8 is a step sequence diagram showing one example of integration of the acoustic frequency detection system 300 with the electronic control device 900. As described above, the electronic control device 900 initiates an automatic priming operation when the sensor 242 detects connection of the SUDS 190 to the MUDS 130. During the priming operation, the acoustic frequency detection system 300, via the frequency detector 310, generates an electrical signal based on the frequency data of the sonic, infrasonic, or ultrasonic wave emitted from the SUDS 190, and the electronic control device 900 determines the status of the SUDS 190 based on the frequency data of the sonic, infrasonic, or ultrasonic wave. If the frequency of the sonic, infrasonic, or ultrasonic wave is within a predetermined range of frequencies corresponding to a frequency of air being expelled from the SUDS 190, the at least one processor of the electronic control device 900 determines that air is being expelled from the SUDS 190 and that the SUDS 190 was replaced prior to the instant priming operation. The electronic control device 900 then proceeds with a fluid delivery operation, and may issue an alert or message via the sensory indicator 330 and/or the one or more user interfaces 124 of the fluid injector system 100. If the frequency of the sonic, infrasonic, or ultrasonic wave is outside the predetermined range of frequencies corresponding to a frequency of air being expelled from the SUDS 190, the at least one processor of the electronic control device 900 determines that air is not being expelled from the SUDS 190 for any number of reasons, such as that the SUDS 190 was not replaced prior to the instant priming operation, the MUDS 130 or SUDS 190 is functioning incorrectly, or the SUDS 190 is improperly connected to the MUDS 130. The electronic control device 900 may then issue an alert or message via the sensory indicator 330 and/or the one or more user interfaces 124 of the fluid injector system 100. In some examples, the electronic control device 900 may also halt the fluid delivery operation according to a preprogrammed protocol, such as until the SUDS 190 is replaced.

In some examples, the at least one processor of the electronic control device 900 may be configured to continuously collect data and generate a log of all priming operations to track the replacement, or lack thereof, of the SUDS 190 with each priming operation. In particular, the at least one processor of the electronic control device 900 may be configured to store a data entry on a computer-readable media, the data entry including the time at which each priming operation occurred and whether or not the SUDS 190 had been primed and/or used prior to the instant priming operation. The data entries may then be cross-referenced against a staff schedule to determine the work practices of individual users. In this manner, compliance with safe hygienic practices may be encouraged and enforced.

In some examples, the acoustic frequency detection system 300 may be configured to detect properties of the tubing 208 based on the whistle emitted from the SUDS 190. For example, the length of the tubing 208 may be determined based on the duration of air being expelled from the SUDS 190. In particular, the at least one processor of the electronic control device 900 may determine the duration for which the frequency of the sonic, infrasonic, or ultrasonic wave emitted from the SUDS 190 is within the predetermined range of frequencies of air expelled from the SUDS 190. The determined duration may be divided from a known or measured flow rate of fluid through the tubing 208 to determine the length of the tubing 208. With the length of the tubing 208 determined, the at least one processor of the electronic control device 900 may determine the amount of additional priming necessary to prime components downstream of the element of the SUDS 190 which emits the whistle. In other examples, the material of the tubing 208 may be determined based on the frequency of the sonic, infrasonic, or ultrasonic wave.

While several examples of single-use disposable set connectors are shown in the accompanying drawings and described hereinabove in detail, other examples will be apparent to, and readily made by, those skilled in the art without departing from the scope and spirit of the disclosure. For example, it is to be understood that this disclosure contemplates that, to the extent possible, one or more features of any example can be combined with one or more features of any other example. Accordingly, the foregoing description is intended to be illustrative rather than restrictive.

We claim:

1. A fluid injector system, comprising:
   a powered fluid injector;
   a connection port configured to form a releasable fluid connection with a single-use disposable set for use in delivering fluid to a patient, the single-use disposable set having a fluid inlet port, a waste outlet port, a tubing connected at a first end thereof to the fluid inlet port and at a second end thereof to a connector configured for connection to the waste outlet port and at least one check valve located between the fluid inlet port and the connector or within an additional fluid path set connected to the connector to facilitate fluid delivery to the patient; and
   an acoustic frequency detection system having a detector associated with the connection port and configured to generate a signal in response to a sonic, infrasonic, or ultrasonic wave emitted from the single-use disposable set as a result of air flowing through the at least one check valve during a priming operation of the single-use disposable set while the air is being expelled therefrom.

2. The fluid injector system of claim 1, wherein the detector is configured to generate the signal if a frequency of the sonic, infrasonic, or ultrasonic wave emitted from the single-use disposable set is within a predetermined range of frequencies, the predetermined range of frequencies corresponding to a predetermined range of frequencies of air expelled from the single-use disposable set during the priming operation.

3. The fluid injector system of claim 1, further comprising an indicator configured to:
   receive the signal generated by the detector; and
   based on the received signal, generate an alert.

4. The fluid injector system of claim 3, wherein the indicator comprises a light and wherein generating the alert comprises illuminating the light.

5. The fluid injector system of claim 3, wherein the indicator comprises a speaker and wherein generating the alert comprises emitting an audible sound from the speaker.

6. The fluid injector system of claim 1, further comprising:
   an electronic control device configured to control filling and delivery operations of the powered fluid injector, the electronic control device comprising at least one processor programmed or configured to receive the signal generated by the detector,
wherein the signal generated by the detector comprises frequency data of the sonic, infrasonic, or ultrasonic wave emitted from the single-use disposable set during the priming operation.

7. The fluid injector system of claim 6, wherein the at least one processor of the electronic control device is further programmed or configured to:
   determine, based on the frequency data, whether the frequency of the sonic, infrasonic, or ultrasonic wave emitted from the single-use disposable set is outside a predetermined range of frequencies, the predetermined range of frequencies corresponding to a predetermined range of frequencies of air expelled from the single-use disposable set during the priming operation; and
   determine, if the frequency of the sonic, infrasonic, or ultrasonic wave emitted from the single-use disposable set is outside the predetermined range of frequencies, whether the single-use disposable set was used during a fluid injection procedure prior to the priming operation.

8. The fluid injector system of claim 6, wherein the at least one processor of the electronic control device is further programmed or configured to determine, based on a duration of the sonic, infrasonic, or ultrasonic wave, a length of the tubing.

9. The fluid injector system of claim 8, wherein the at least one processor of the electronic control device is further programmed or configured to determine, based on at least one of the length of the tubing and the duration of the sonic, infrasonic, or ultrasonic wave, an amount of fluid necessary to prime the single-use disposable set.

10. The fluid injector system of claim 7, further comprising a user interface having a display,
   wherein the at least one processor of the electronic control device is further programmed or configured to display a message on the user interface if the at least one processor determines that the single-use disposable set was used during the fluid injection procedure prior to the priming operation.

11. The fluid injector system of claim 7, wherein the at least one processor of the electronic control device is further programmed or configured to prevent a subsequent fluid injection procedure if the at least one processor determines that the single-use disposable set was used during the fluid injection procedure prior to the priming operation.

12. The fluid injector system of claim 7, wherein the at least one processor of the electronic control device is further programmed or configured to:
   store a data entry on a computer-readable media if the at least one processor determines that the single-use disposable set was used during the fluid injection procedure prior to the priming operation.

13. The fluid injector system of claim 12, wherein the data entry comprises a time at which the priming operation was performed.

14. The fluid injector system of claim 12, wherein the data entry comprises identification information of a user of the fluid injector system.

15. The fluid injector system of claim 7, wherein the at least one processor of the electronic control device is further programmed or configured to permit a subsequent fluid injection procedure if the at least one processor determines that the single-use disposable set was not used during the fluid injection procedure prior to the priming operation.

16. A method for detecting multiple uses of a single-use disposable set connected to a fluid injector system, the method comprising:
   priming the single-use disposable set with a medical fluid, the single-use disposable set being connectable to a connection port of the fluid injector system to enable the single-use disposable set to be primed with the medical fluid;
   detecting, via an acoustic frequency detection system, at least one of a frequency and duration of a sonic, infrasonic, or ultrasonic wave emitted from the single-use disposable set when air is flowing through at least one check valve thereof during a priming operation of the single-use disposable set while the air is being expelled therefrom; and
   determining, based on at least one of the frequency and duration of the sonic, infrasonic, or ultrasonic wave, whether the air is expelled from the single-use disposable set during the priming operation.

17. The method of claim 16, further comprising generating an alert if the frequency of the sonic, infrasonic, or ultrasonic wave is outside a predetermined range of frequencies, the predetermined range of frequencies corresponding to a predetermined range of frequencies of air expelled from the single-use disposable set.

18. The method of claim 17, wherein the alert comprises a message displayed on a user interface of the fluid injector system.

19. The method of claim 16, further comprising preventing a subsequent fluid injection procedure if the frequency of the sonic, infrasonic, or ultrasonic wave is outside a predetermined range of frequencies, the predetermined range of frequencies corresponding to a predetermined range of frequencies of air expelled from the single-use disposable set.

20. The method of claim 16, further comprising storing, on a computer-readable media, a data entry if the frequency of the sonic, infrasonic, or ultrasonic wave is outside a predetermined range of frequencies, the predetermined range of frequencies corresponding to a predetermined range of frequencies of air expelled from the single-use disposable set.

* * * * *

UNITED STATES PATENT AND TRADEMARK OFFICE
CERTIFICATE OF CORRECTION

PATENT NO. : 11,529,456 B2
APPLICATION NO. : 16/481916
DATED : December 20, 2022
INVENTOR(S) : Volkar et al.

Page 1 of 1

It is certified that error appears in the above-identified patent and that said Letters Patent is hereby corrected as shown below:

In the Specification

In Column 6, Lines 62-63, delete "When used in relation to a syringe of a," and insert -- When used in relation to a syringe of a multi-use disposable set, --, therefor.

Signed and Sealed this
Twenty-seventh Day of June, 2023

Katherine Kelly Vidal
*Director of the United States Patent and Trademark Office*